United States Patent
Mullor Sanjosé et al.

(10) Patent No.: US 11,013,732 B2
(45) Date of Patent: May 25, 2021

(54) USE OF MACROAZAPYRIDINOPHANES METAL COMPLEXES IN THE TREATMENT OF DISEASES

(71) Applicant: BIONOS BIOTECH, S.L, Valencia (ES)

(72) Inventors: José Luis Mullor Sanjosé, Valencia (ES); Rafael Vázquez Manrique, Valencia (ES); David González Fernández, Valencia (ES)

(73) Assignee: BIONOS BIOTECH, S.L., Valencia (ES)

( * ) Notice: Subject to any disclaimer, the term of this patent is extended or adjusted under 35 U.S.C. 154(b) by 0 days.

(21) Appl. No.: 16/621,782

(22) PCT Filed: Jul. 3, 2018

(86) PCT No.: PCT/EP2018/068010
§ 371 (c)(1),
(2) Date: Dec. 12, 2019

(87) PCT Pub. No.: WO2019/007996
PCT Pub. Date: Jan. 10, 2019

(65) Prior Publication Data
US 2020/0101062 A1 Apr. 2, 2020

(30) Foreign Application Priority Data
Jul. 4, 2017 (EP) .................................. 17382429

(51) Int. Cl.
*A61K 31/4706* (2006.01)
*A61P 25/28* (2006.01)
*A61K 33/26* (2006.01)
*A61K 33/30* (2006.01)
*A61K 33/32* (2006.01)
*A61K 33/34* (2006.01)
*A61K 31/4709* (2006.01)

(52) U.S. Cl.
CPC ...... *A61K 31/4706* (2013.01); *A61K 31/4709* (2013.01); *A61K 33/26* (2013.01); *A61K 33/30* (2013.01); *A61K 33/32* (2013.01); *A61K 33/34* (2013.01); *A61P 25/28* (2018.01)

(58) Field of Classification Search
CPC ............ A61K 31/4706; A61K 31/4709; A61K 33/26; A61K 33/30; A61K 33/32; A61K 33/34; A61P 25/28
See application file for complete search history.

(56) References Cited

U.S. PATENT DOCUMENTS

| | | |
|---|---|---|
| 9,145,386 B2 | 9/2015 | García-España Monsonís et al. |
| 9,750,677 B2 | 9/2017 | García-España Monsonís et al. |
| 2017/0007521 A1* | 1/2017 | Garcia-Espana Monson S .......... A23L 3/358 |

FOREIGN PATENT DOCUMENTS

| | | | |
|---|---|---|---|
| EP | 2492270 A2 | 8/2012 | |
| WO | WO-2013087965 A1 * | 6/2013 | ............. A61P 33/02 |
| WO | 2015124824 A1 | 8/2015 | |

OTHER PUBLICATIONS

Castillo; Dalton Trans., 2012, 41,5617-5624. (Year: 2012).*
Clares; Chem. Commun., 2011,47, 5988-5990. (Year: 2011).*
Frake; J Clin Invest. 2015, 125, 65-74. (Year: 2015).*
Launay; Acta Neuropathologica 2015, 129, 399—415. (Year: 2015).*
Levine; Cell 2008, 132, 27-42. (Year: 2008).*
Macarthur; Critical Care Medicine 2003, 31, 237-245. (Year: 2003).*
Pan; Brain, 2008, 131, 1969-1978. (Year: 2008).*
Towers; EBioMedicine 2016, 14, 15-23. (Year: 2016).*
Vilchez; Nature Communications 2014, 5, Article No. 5659. (Year: 2014).*
Bonetta; Chem. Eur.J. 2018, 24, 5032-5041. (Year: 2018).*
Iranzo; Bioorganic Chemistry 2011, 39, 73-87. (Year: 2011).*
Pong; Expert Opinion on Biological Therapy, 2003, 3, 127-139. (Year: 2003).*

(Continued)

*Primary Examiner* — Daniel R Carcanague

(74) *Attorney, Agent, or Firm* — Tristan A. Fuierer; Olive Law Group, PLLC

(57) ABSTRACT

Metal complexes comprising a compound of general formula (I)

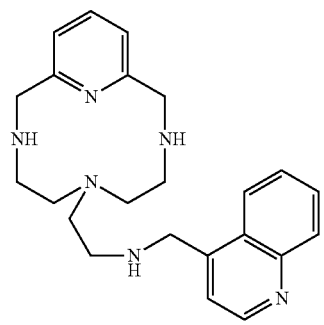

Formula (I)

and at least one metal ion, for use in the treatment of diseases related to the accumulation of intracellular deposits and/or diseases related to defective autophagy and/or defective proteasome activity is disclosed. Compositions comprising said metal complexes comprising a compound of general formula (I) and at least one metal ion, for use in the treatment of diseases related to the accumulation of intracellular deposits and/or diseases related to defective autophagy and/or defective proteasome activity are also disclosed.

13 Claims, 8 Drawing Sheets

(56) References Cited

OTHER PUBLICATIONS

International Search Report, dated Oct. 15, 2018.
Aguado, Carmen, et al.; "Laforin, the most common protein mutated in Lafora disease, regulates autophagy," Human Molecular Genetics, 2010, vol. 19, pp. 2867-2876; doi:10.1093/hmg/ddq190.
Knecht, Erwin, et al.; "Impaired autophagy in Lafora disease," Autophagy, 2010, DOI: 10.4161/auto6.7.13308.
Criado, Olga, et al.; "Lafora bodies and neurological defects in malin-deficient mice correlate with impaired autophagy," Human Molecular Genetics, 2012, vol. 21, pp. 1521-1533, doi:101093/hmg/ddr590.
Knecht, Erwin, et al.; "Malin knockout mice support a primary role of autophagy in the pathogenesis of Lafora disease," Autophagy, 2012, vol. 8, pp. 701-703, doi: 10.4161/auto.19522.
Moruno-Manchón, Jose Félix, et al; "Glucose induces autophagy under starvation conditions by a p38 MAPK-dependent pathway," Biochem. J., 2013, vol. 449, pp. 497-506, doi: 10.1042/BJ20121122.
Fuertes, Graciela, et al.; "Changes in the proteolytic activities of proteasomes and lysosomes in human fibroblasts produced by serum withdrawal, amino-acid deprivation and confluent conditions," Biochem. J., 2003, vol. 375, pp. 75-86, doi: 10.1042/BJ20030282.
Clares, M. Paz, et al.; "Mn(II) complexes of scorpiand-like ligands. A model for the MnSOD active centre with high in vitro and in vivo activity," Journal of Inorganic Biochemisty, 2015, vol. 143, pp. 1-8.
Olmo, F., et al.; "Synthetic single and double aza-scorpiand macrocycles acting as inhibitors of the antioxidant enzymes iron superoxide dismutase and trypanothione reductase in Trypanosoma cruzi with promising results in a murine model," RSC Advances, 2014, vol. 4, pp. 65108-65120, doi: 10.1039/c4ra09866h.
Nguyen, Trent, et al.; "Clioquinol down-regulates mutant huntingtin expression in vitro and mitigates pathology in a Huntington's disease mouse model," PNAS, 2005, vol. 102, pp. 11840-11845, www.pnas.org/cgi/doi/10.1073pnas.0502177102.

* cited by examiner

FIGURE 5A
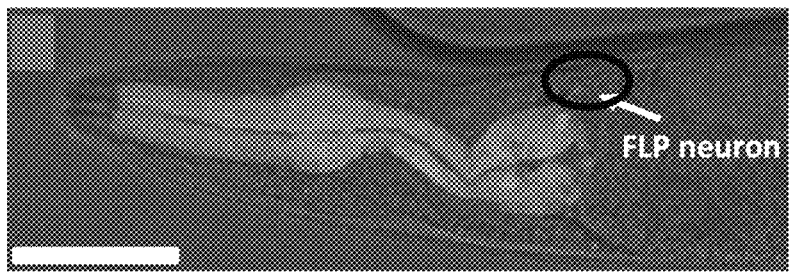
FIGURE 5B
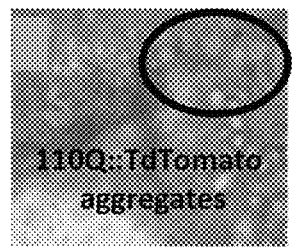
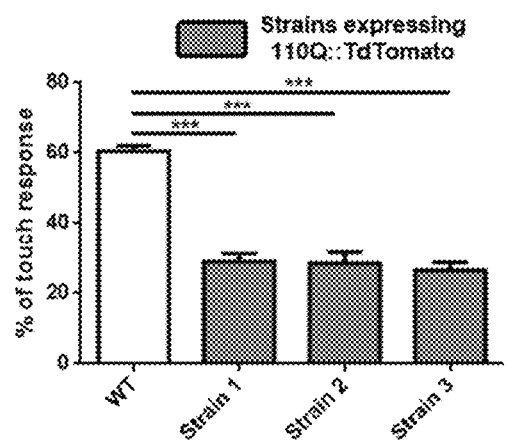
FIGURE 5C
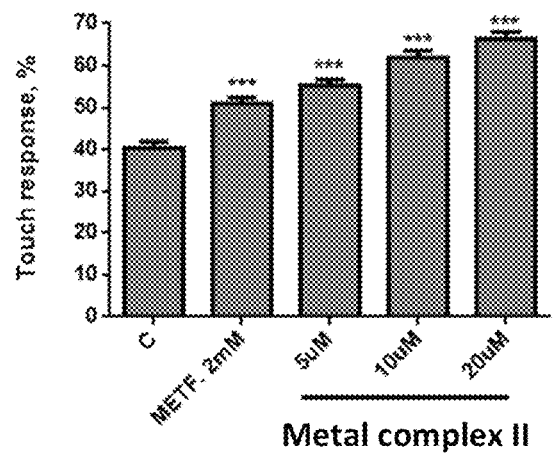
FIGURE 5D

USE OF MACROAZAPYRIDINOPHANES METAL COMPLEXES IN THE TREATMENT OF DISEASES

CROSS-REFERENCE TO RELATED APPLICATIONS

This application is filed under the provisions of 35 U.S.C. § 371 and claims the priority of International Patent Application No. PCT/EP2018/068010, filed on 3 Jul. 2018 entitled "USE OF MACROAZAPYRIDINOPHANES METAL COMPLEXES IN THE TREATMENT OF DISEASES" in the name of Jose Luis MULLOR SANJOSÉ, et al., which claims priority to European Patent Application No. 17382429.3 filed on 4 Jul. 2017, both of which are hereby incorporated by reference herein in their entirety.

FIELD OF THE INVENTION

The present invention relates to metal complexes of macroazapyridinophanes, and compositions thereof, for use in the treatment and prevention of diseases related to the accumulation of intracellular deposits and/or diseases related to defective autophagy and/or defective proteasome activity.

BACKGROUND OF THE INVENTION

Lysosomes and proteasomes are the two major cellular paths to eliminate accumulation of intracellular deposits. While lysosomes are critical in breaking down proteins, nucleic acids or lipids into cells through endocytosis, in a process known as autophagy, proteasomes are the main responsible for intracellular protein in eukaryotes.

Autophagy is a lysosomal degradative process used to recycle obsolete cellular constituents and eliminate damaged organelles and protein aggregates. The process of autophagy comprises multiple steps: after the induction of autophagy, parts of the cytoplasm, which can include entire organules, are captured by a double membrane, forming an autophagosome. After that, autophagosomes merge with endosomes and lysosomes forming autolysosomes. It is then that the complete digestion of the organules and macromolecules takes place. The elongation of the autophagosomal membrane is controlled mainly by two systems of protein conjugation. One system implies the conjugation of Atg12 and Atg5 and the other implies the conversion of the cytosolic form of LC3, known as LC3-I, to the lipidic form, known as LC3-II, which is associated to the autophagosomes membrane. The level of the LC3-II protein is nowadays the most accepted and used biomarker of autophagy activity.

On the other hand, several studies have demonstrated that during aging proteostasis collapses leading to the accumulation of unfolded, misfolded or aggregated proteins, which causes many age-related diseases. One of the main mechanisms for the maintenance of the proteome is the proteasome system, which ensures the removal of damaged or misfolded proteins, and therefore playing a central role at delaying aging.

Finally, several diseases present defects in autophagy and proteasome activity, causing cells to accumulate proteins, lipids or other molecules. In fact, neurons are cells particularly vulnerable to impaired autophagy or proteasome activity. For example, mutant Huntingtin, the protein responsible for Huntington's disease, is expressed ubiquitously in mammals. However, only the nervous system suffers a substantial impairment after this molecule collapses into aggregates and accumulate into and around the nucleus of neurons. Every other tissue and type of cell remains apparently unaffected. Hence, diseases presenting protein deposits or accumulation clearly have a cellular problem eliminating those internal deposits either through autophagy or proteasome activity.

Thus, there is a need to treat diseases which present accumulation of intracellular deposits, wherein said accumulation is due to metabolic deficiencies resulting in an abnormal accumulation of those deposits and wherein the normal cellular autophagy or proteasome activity is not able to remove them, or diseases wherein said accumulation is due to a defective autophagy or proteasome activity.

Granted patents EP2492270 and U.S. Pat. No. 9,145,386 refer to metal complexes comprising a compound described below as A or B. Said compound comprises a macrocyclic polyazapyridinophane central structure with a quinolone heterocycle attached to said central structure and wherein said quinolone heterocycle is bonded by the 4-position to a methylene group (or bridge) which is bonded in turn to the —NH group of a ethylamine chain linked to said triazapyridinophane central structure (shown as A below), or, alternatively, wherein said quinolone heterocycle is bonded to by the 2-position to the methylene group which is bonded in turn to the —NH group of a ethylamine chain linked to said triazapyridinophane central structure (shown as B below).

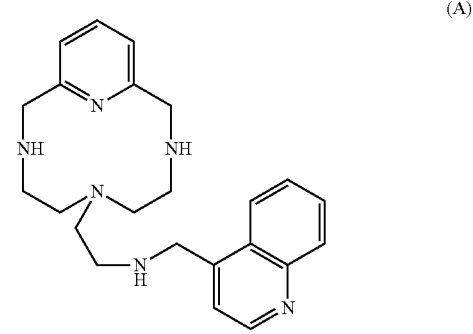

(A)

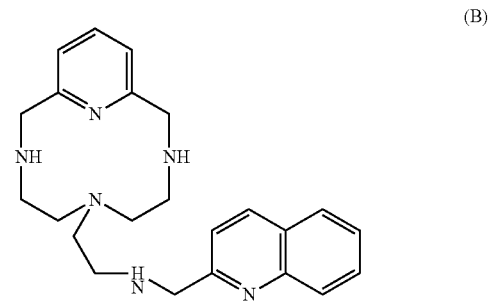

(B)

Said family of metal complexes, comprising the compounds shown as A or B above, are useful, according to the cited patents, to treat therapeutically diseases "whose aetiology is rooted in disturbances in the activity of, or a deficiency in endogenous SOD" (c.f. EP2492270 [0001]).

BRIEF DESCRIPTION OF THE INVENTION

The present invention relates to a metal complex comprising a compound of general formula (I)

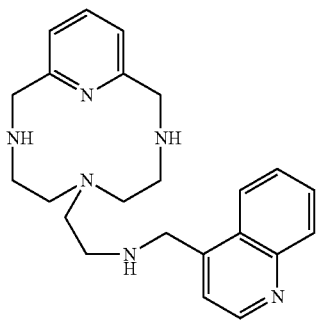

Formula (I)

and at least one metal ion, for use in treatment of diseases related to the accumulation of intracellular deposits, and/or diseases related to defective autophagy and/or defective proteasome activity.

The metal complexes disclosed herein feature thus a triazapyridinophane central linked by the 4-position of a quinolone moiety.

The experimental data disclosed in the present description, relates only to a selection of said family of metal complexes, wherein the quinolone heterocycle featured in said family of metal complexes is bonded by the 4-position to the triazapyridinophane central structure (shown as A).

One embodiment disclosed refers to the metal complexes described above herein for use in the treatment of diseases related to the accumulation of intracellular deposits and/or diseases related to defective autophagy and/or defective proteasome activity, wherein said metal ion is a divalent metal ion.

Another embodiment disclosed refers to the metal complexes described above herein for use in the treatment of diseases related to the accumulation of intracellular deposits and/or diseases related to defective autophagy and/or defective proteasome activity, wherein said divalent metal ion can be selected independently from Cu(II), Fe(II), Zn(II) or Mn(II).

Another embodiment of the above disclosed metal complexes for use in the treatment of diseases related to the accumulation of intracellular deposits and/or diseases related to defective autophagy and/or defective proteasome activity, is metal complex (II) which comprises a compound of formula (I) and Mn(II).

The experimental data disclosed shows that activation of autophagy and/or proteasome activity is present only for a specific selection of the family of triazapyridinophane metal complexes disclosed in the above-mentioned patent documents (EP2492270, U.S. Pat. No. 9,145,386 and WO 2015124824 A1). In fact, the present invention relates to the specific selection of metal complexes, wherein the quinolone moiety is linked to the triazapyridinophane central structure by the 4-position, for use in the treatment of diseases related to the accumulation of intracellular deposits and/or diseases related to defective autophagy and/or defective proteasome activity.

Additionally, one embodiment of present invention refers to compositions comprising an effective amount of a metal complex comprising a compound of general formula (I), as described above herein, and at least one metal ion; together with at least one excipient or carrier, for use in the treatment of diseases related to the accumulation of intracellular deposits, and/or diseases related defective autophagy and/or defective proteasome activity. Preferably said metal ion is a divalent metal ion, more preferably said divalent metal ion is can be selected independently from Cu(II), Fe(II), Zn(II) or Mn(II), and even more preferably is Mn(II).

BRIEF DESCRIPTION OF THE FIGURES

FIG. 1A shows the effect of metal complex (II) in LC3-II levels for control cell lines (C1 and C2) and Lafora patients cell lines (L1, L2 and M1) in complete and fast media (Krebs-Henseleit). FIG. 1B shows the effect of metal complex (II) in LC3-II levels for control cell lines (C1 and C2) and L3 and M1 Lafora cell lines in complete and fast media.

FIG. 3: In vitro studies to show the proteasome chymotrypsin-like activation with metal complex (II) in human dermal fibroblasts. Results are measured in relative luminescence units (RLUs) normalized to the control.

FIG. 5A shows a confocal image of the head of a transgenic worm (*C. elegans*) showing 110Q::TdTomato expression in FLP mechanosensory neurons (shown circled). The tissue in light grey is the marker for transgenesis (i.e. green fluorescent protein (GFP) expressed in the pharynx). FIG. 5B shows a confocal image showing the FLP neurons expressing 110Q::TdTomato aggregates (shown circled). FIG. 5C shows touch assays on three independent strains expressing 110Q::TdTomato showing neuronal impairment (lower mechanosensation than wildtype animals). FIG. 5D shows how metal complex (II) is able to rescue neuronal impairment due to 110Q::TdTomato expression in a dose-dependent manner. The test was carried out using non-treated animals (expressing 110Q::TdTomato showing neuronal impairment) as a control C. Results in FIGS. 5C and 5D presented as % of individuals showing touch response. Metformin (METF) was used as a positive control

DETAILED DESCRIPTION

Figure 1A:
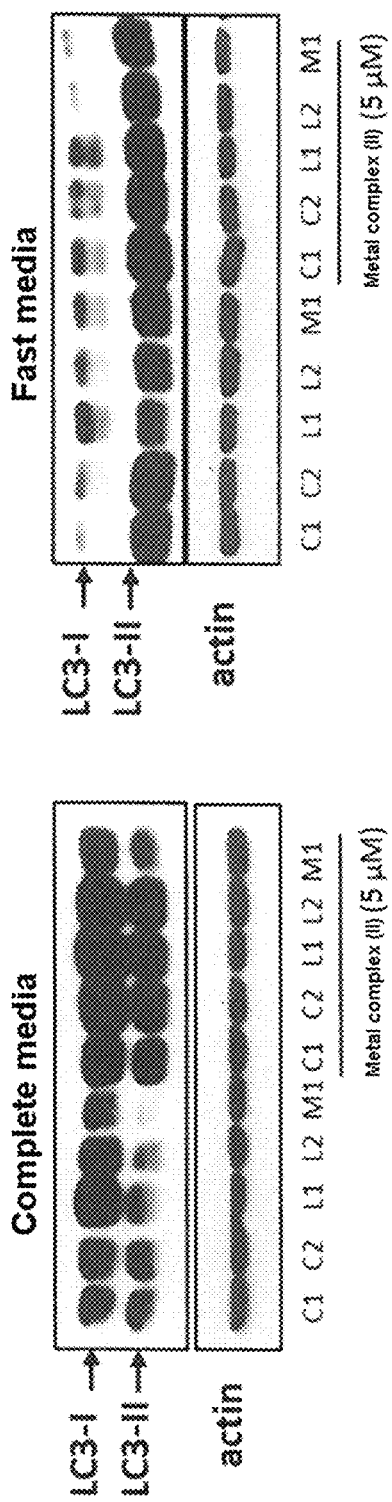
FIGS. 1A and 1B: Levels of LC3-II on human fibroblasts in the presence or absence of metal complex (II).

The present invention refers therefore, to a metal complex comprising a compound of general formula (I)

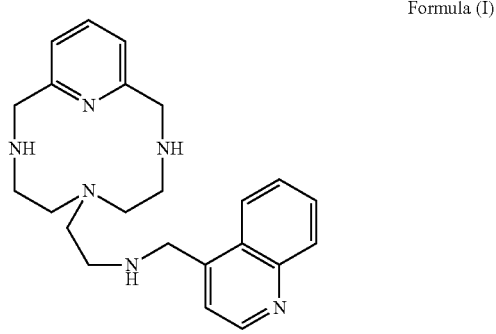

Formula (I)

and at least one metal ion, for use in treatment of diseases related to the accumulation of intracellular deposits, and/or diseases related to defective autophagy and/or defective proteasome activity.

As described herein, a metal complex refers to a molecular association of a compound with at least one metal ion, in particular to a molecular association of the compound of general formula (I) with at least one metal ion.

One embodiment of present invention refers to the metal complexes comprising a compound of Formula (I) and at least one metal ion, for use in the treatment of diseases related to the accumulation of intracellular deposits and/or diseases related to defective autophagy and/or defective proteasome activity, wherein said metal ion is a divalent metal ion.

Another embodiment of present invention refers to the metal complexes comprising a compound of Formula (I) and at least one metal ion, for use in the treatment of diseases related to the accumulation of intracellular deposits and/or diseases related to defective autophagy and/or defective proteasome activity, wherein said divalent metal ion is independently selected from Cu(II), Fe(II), Zn(II) or Mn(II).

In another embodiment of present invention, the metal complex is metal complex (II) which comprises a compound of formula (I) and Mn(II).

In the context of present invention the diseases related to the accumulation of intracellular deposits and/or diseases related to defective autophagy and/or defective proteasome activity refer, but are not limited to Huntington disease, Prion disease, Focal segmental glomerulosclerosis, diseases related to an AAT deficiency (Alpha-1 antitrypsin deficiency), sphingolipidoses, Niemann-Pick type C disease (NPC), Wolman disease and Cholesteryl Ester Storage Diseases (CESD), glycogen storage diseases, galactosemia, hereditary fructose intolerance, muccopolysaccharidoses, disorders of pyruvate metabolism, phosphoglycerate kinase deficiency, Lafora disease, Adrenoleukodystrophy, Autophagic Vacuolar Myopathies, Danon's disease, Cerebral Cavernous Malformation (CCM), Granular corneal dystrophy type 2 (GCD2), Chronic Kidney Disease (CKD), inherited muscle diseases as Bethlem myopathy, Ullrich congenital muscular dystrophy and Myosclerosis, inclusion body myositis; viral infections as HIV, adenovirus, hepatitis B or HTLV; Sjogren's syndrome; sepsis or metabolic acidosis.

In particular, an embodiment of present invention refers to a metal complex comprising a compound of Formula (I) and at least one metal ion, for use in treatment of diseases related to the accumulation of intracellular deposits and/or defective autophagy and/or defective proteasome activity, according to present invention, wherein said diseases are independently selected from Huntington disease, Prion disease, cataracts, Focal segmental glomerulosclerosis, diseases related to an AAT deficiency, sphingolipidoses, Niemann-Pick type C disease (NPC), Wolman disease and Cholesteryl Ester Storage Diseases (CESD), glycogen storage diseases, galactosemia, hereditary fructose intolerance, muccopolysaccharidoses, disorders of pyruvate metabolism, phosphoglycerate kinase deficiency, Lafora disease, Adrenoleukodystrophy, Autophagic Vacuolar Myopathies, Danon's disease, Cerebral Cavernous Malformation (CCM), Granular corneal dystrophy type 2 (GCD2), Chronic Kidney Disease (CKD), Bethlem myopathy, Ullrich congenital muscular dystrophy, Myosclerosis, inclusion body myositis, HIV, adenovirus, hepatitis B, HTLV; Sjogren's syndrome, sepsis or metabolic acidosis. Preferably said diseases are independently selected from Lafora disease, Adrenoleukodystrophy or Huntington disease. More preferably said disease is Lafora disease or Huntington disease.

The metal complexes comprising a compound of Formula (I) and at least one metal ion disclosed herein, stimulate or activate autophagy and proteasome activity, in cells presenting defective autophagy and/or defective proteasome activity. The metal complexes disclosed herein are also capable of reducing the symptoms of diseases presenting defective autophagy and/or defective proteasome activity.

One embodiment of present invention refers to the metal complexes comprising a compound of Formula (I) and at least one metal ion, described above herein for use in the treatment of diseases related to the accumulation of intracellular deposits and/or diseases related to defective autophagy and/or defective proteasome activity, wherein said diseases are age-related diseases.

For the purposes of present description, age-related diseases are diseases associated with increasing senescence which in turn is associated with cellular aging and accumulation of cellular damage, in particular, the accumulation of intracellular deposits which are lipid, carbohydrate or protein deposits.

In the context of this disclosure said age-related diseases, which in turn are associated with accumulation of lipid, carbohydrate or protein deposits refer, but are not limited to diseases related to an AAT deficiency (Alpha-1 antitrypsin deficiency), Huntington disease, Prion disease, Focal segmental glomerulosclerosis, sphingolipidoses, Niemann-Pick type C disease (NPC), Wolman disease and Cholesteryl Ester Storage Diseases (CESD), glycogen storage diseases, galactosemia, hereditary fructose intolerance, muccopolysaccharidoses, disorders of pyruvate metabolism or phosphoglycerate kinase deficiency.

Another embodiment of present invention refers to the metal complexes comprising a compound of Formula (I) and at least one metal ion, described above herein, for use in the treatment of diseases related to the accumulation of intracellular deposits and/or diseases related to defective autophagy and/or defective proteasome activity, wherein said disease is independently selected from Lafora disease or Huntington disease.

One embodiment of present invention refers to the metal complexes comprising a compound of Formula (I) and at least one metal ion, described above herein, for use in the treatment of diseases which present accumulation of intracellular deposits. In a preferred embodiment said diseases are selected from Lafora disease, Adrenoleukodytrophy or Huntington disease, more preferably Lafora disease or Huntington disease.

Lafora disease, also named Lafora progressive myoclonic epilepsy or MELF is an autosomal recessive genetic disorder characterized by the presence of inclusion bodies (Lafora bodies), within the cytoplasm of the cells of the heart, liver, muscle and skin. Lafora patients present mutations in Laforin or Malin proteins.

Figure 1B:
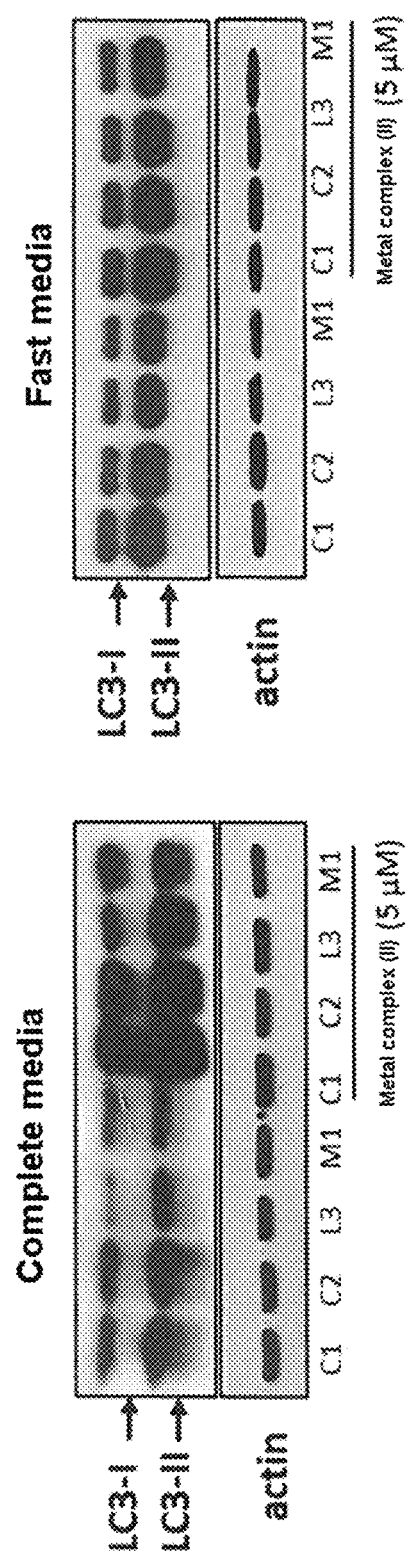
Figure 1C:
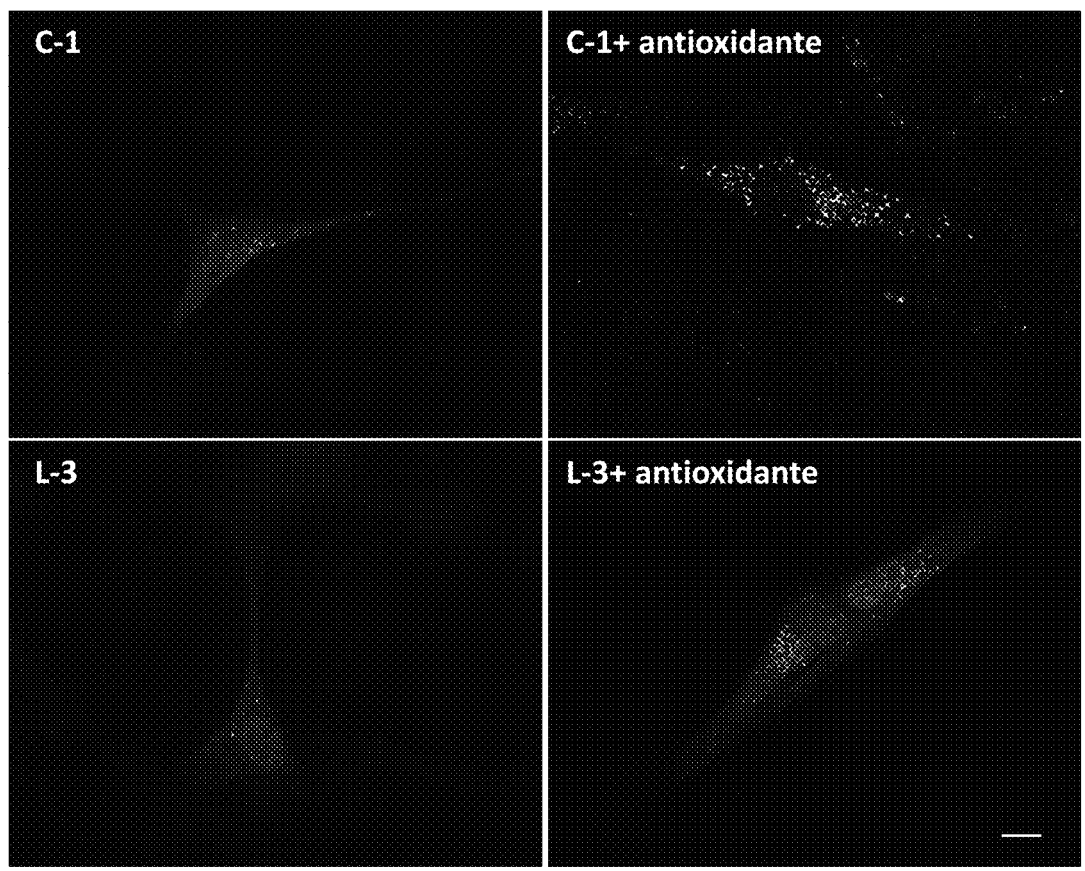
FIG. 1C shows human fibroblast from Lafora patients (shown as L-3) and healthy human fibroblasts (shown as C-1), transfected with fluorescent GFP-LC3, tested in absence or presence of metal complex (II) at 5 µM during 6 hours. The visible points show the autophagic vacuoles. The white line at the bottom of the figure is used for reference and represents 10 µm.
Figure 2:
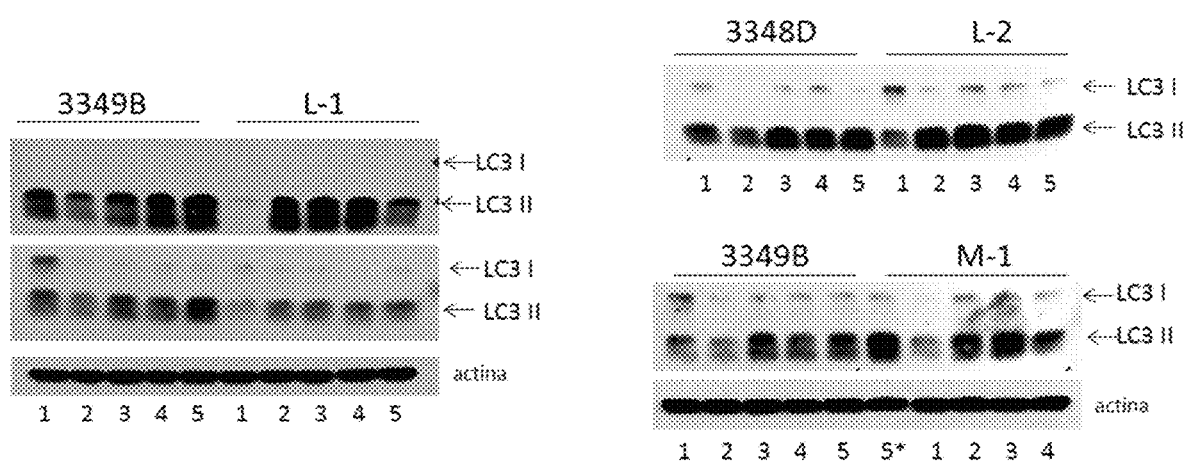
FIG. 2: Levels of LC3-II on human fibroblasts (cell lines 3349B and 3348D) healthy or with mutations in Laforin (L1 for Laforin mutations on 3349B and L2 for Laforin mutations on 3348D) and Malin (M1 for Malin mutations on 3349B) tested in the absence (labelled as 1) or presence of metal complex (II) at 1 µM, 5 µM and 10 µM concentrations (labelled as 2, 3 and 4 respectively). Rapamycin was used as a positive control (labelled as 5). Label 5* is an error of loading.

The metal complexes comprising a compound of Formula (I) and at least one metal ion, disclosed herein, activate autophagy in cells of patients of Lafora disease with mutations in Laforin and Malin proteins which present deficient autophagy, as shown in EXAMPLE 1 (FIGS. 1 and 2). In fact, in EXAMPLE 1 fibroblasts from healthy individuals and fibroblasts from Lafora disease patients were tested. Results show that all fibroblasts have greater levels of LC3-II protein after the treatment with the metal complex (II), wherein the amount of LC3-II indicates the level of autophagy activation (FIGS. 1 and 2).

A first test was carried out with complete media and with fasting media. Partially removing the nutrients from the culture media emulates a cell fasting state (fasting media) and provokes the cell to activate autophagy to obtain energy from degrading internal structures.

The deficient autophagy present in Lafora patients is shown in FIG. 1A, FIG. 1B, wherein non-treated cell lines with mutations in Laforin and Malin (L1, L2, L3 or M1) show lower LC3-II level than non-treated control cell lines (C1 and C2) in both complete and fasting media.

Both control fibroblasts and fibroblasts from Lafora patients (FIGS. 1A and 1B) have greater levels of LC3-II protein after the treatment with the metal complex (II), at a concentration of 5 μM during 6 hours.

In fasting media and in absence of metal complex (II), an increment of the level of protein LC3-II is seen when compared to the test done with the same cells in complete media, confirming that autophagy increases in absence of nutrients. The treatment with metal complex (II) increases the levels of LC3-II even further in reference with the non-treated cells, confirming the increase of autophagy levels in the cells treated with metal complex (II).

Another study was carried out testing metal complex (II) at 1, 5 and 10 μM concentrations. Levels of LC3-II on human fibroblasts healthy or in human fibroblasts with mutations in Laforin and Malin were tested in the absence (labelled as 1) or presence of metal complex (II) at 1 μM, 5 μM and 10 μM concentrations (labelled as 2, 3 and 4 respectively). Rapamycin was used as a positive control (labelled as 5). Again, the deficient autophagy present in Lafora patients is seen also in this study in FIG. 2 comparing the level of LC3-II in healthy non-treated cells with non-treated Lafora cells. The results of the test are shown in FIG. 2 wherein metal complex (II) increased autophagy when added to the media, showing higher levels of LC3-II protein on normal human fibroblasts as well as fibroblasts deficient in Laforin or Malin.

Considering that the amount of LC3-II indicates the level of autophagy activation, said data indicates that metal complex (II) stimulates or activates autophagy in healthy cells and in autophagy deficient cells.

Using a different experiment to study the effect on autophagy of the metal complexes herein disclosed, a fluorescence test with transfected cells with GFP-LC3 was done (FIG. 1C). In this experiment, healthy human fibroblasts (control C-1) and fibroblasts from Lafora patients (L-3) were tested in the absence or presence of metal complex (II). Results shown in FIG. 1C indicate that autophagy is increased (measured by the increase of autophagic vacuoles) in presence of metal complex (II), which indicates again that metal complex (II) stimulates or activates autophagy.

Huntington disease is caused by an autosomal dominant mutation in either one of an individual's two copies of a gene called Huntingtin (Htt). The function of Htt in humans is unclear. Expansion of CAG (cytosine-adenine-guanine) triplet repeats in the gene coding for the Huntingtin protein results in an abnormal protein that encodes a long track of glutamines, which is prone to aggregate with itself and with other proteins. This "sticky" condition of mutant Huntingtin (mHtt) interferes with many important neuronal events (e.g. synaptic transmission, axonal transport, transcription, etc.) and gradually damages cells in the brain through mechanisms which are not fully understood. This disease is therefore caused by accumulation of mHtt protein in neurons. Degradation of these deposits through proteasome and/or autophagy activation with the metal complexes disclosed herein results in a recession of the symptoms as shown for *C. elegans*' Huntington disease model in EXAMPLE 3.

Figure 4A:
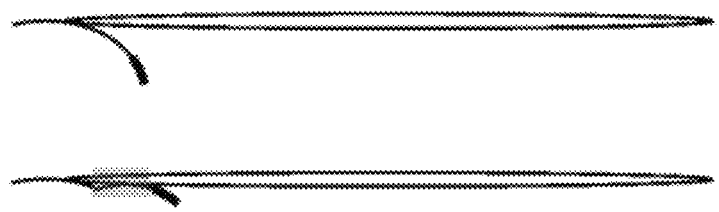
FIG. 4: Graphical representation of the model worm *Caenorhabditis elegans'* (*C. elegans*) and an instrument to test for gentle touch sensitivity (eyebrow hair glued to the end of a toothpick).
Figure 4B:
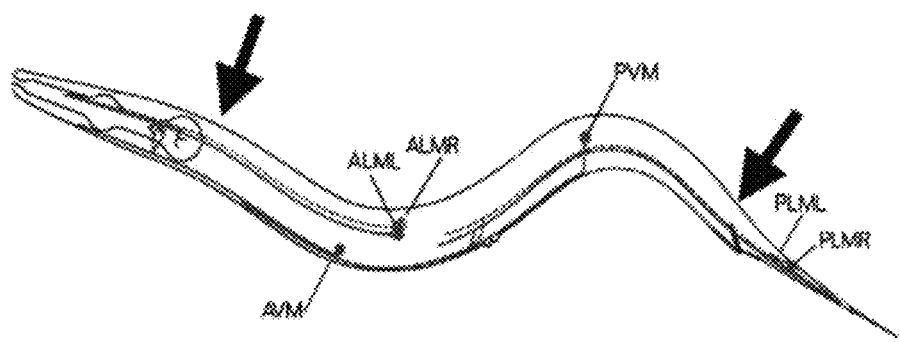

*C. elegans* detect and respond to diverse mechanical stimuli using neuronal circuitry. These stimuli include gentle touch stimulus delivered to the body, harsh touch to the midbody, harsh touch to the head or tail, nose touch and texture. The initial and most generally used method to test for gentle touch sensitivity is to stroke animals with an eyebrow hair that has been glued to the end of a toothpick (FIG. 4).

*C. elegans* animals used in EXAMPLE 3 expressed 110CAG fused in frame with the gene for the red fluorescent protein TdTomato in mechanosensory neurons (110Q::TdTomato), as shown in FIGS. 5A and 5B. Animals expressing 110Q::TdTomato present a neuronal impairment versus the wild type animals (WT), as shown in FIG. 5C, wherein the % of animals showing touch response obtained in the test carried out with the neuronally impaired animals expressing 110Q::TdTomato (three different strains) is significantly lower than the one obtained with WT animals.

Figure 6:
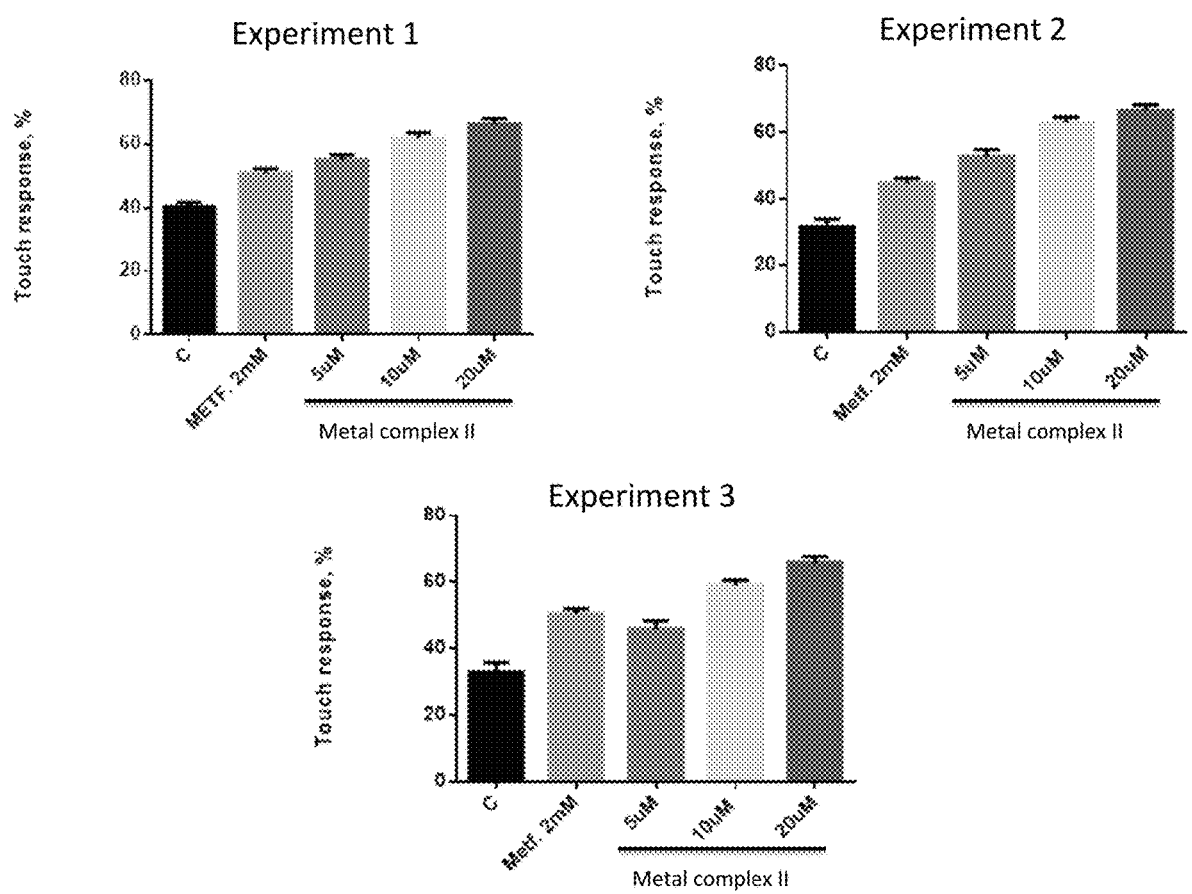
FIG. 6 shows the results of the three replicate tests represented by FIG. 5D wherein metal complex (II) was tested for gentle touch sensitivity at different concentrations in *C. elegans*' Huntington's disease model. The tests were carried out using non-treated animals (expressing 110Q::TdTomato showing neuronal impairment) as a control C. Results presented as % of individuals showing touch response. Metformin (METF) was used as a positive control.

FIG. 5D (and the 3 replicates of said test shown in FIG. 6) shows a significant improvement of the % of individuals showing touch response in animals treated with metal complex (II) when compared to non-treated animals, in a dose dependent manner. Results therefore indicate that the metal complexes of present invention, exemplified by metal complex (II), are able to improve significantly the symptoms shown in *C. elegans*' Huntington disease model expressing 110Q::TdTomato, in a dose dependent manner.

Figure 7:
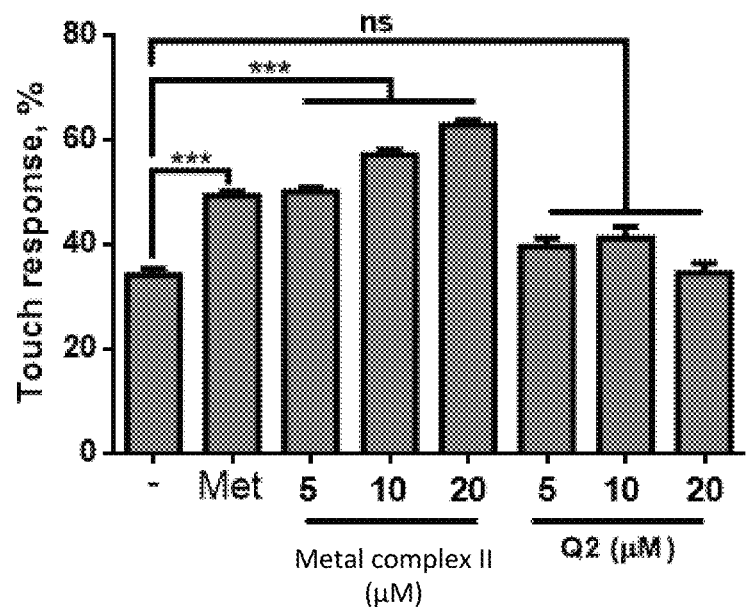
FIG. 7 shows how metal complex (II) is able to rescue neuronal impairment due to 110Q::TdTomato expression in a dose-dependent manner versus compound 2Q which does not produce any significant change in the tested doses. The test was carried out using non-treated animals (expressing 110Q::TdTomato showing neuronal impairment) as a control C. Metformin was used as a positive control. Results presented as % of individuals showing touch response movement.

In contrast to this activity, FIG. 7 does not show a significant improvement of the % touch response in animals treated with 2Q when compared to non-treated animals, and thus, 2Q did not significantly improve the touch response in *C. elegans*' Huntington disease model at any of the doses tested.

The structural differences between 2Q and metal complex (II), are surprisingly responsible for the proteasome and/or autophagy activation provided by the specific family of metal complexes disclosed herein. As described above, the metal complexes comprising a compound of Formula (I) and at least one metal ion, disclosed herein, feature a quinolone moiety bonded by the 4-position to the triazapyridophane central structure of the molecule, whereas 2Q, which is a compound also featuring a triazapyridophane central structure, features instead said quinolone moiety linked by the 2-position.

All the results shown above strongly supports that metal complex (II) is able to rescue the toxic effect produced by 110Q::TdTomato in neurons and significantly increasing the % of animals showing a touch response.

Figure 8:
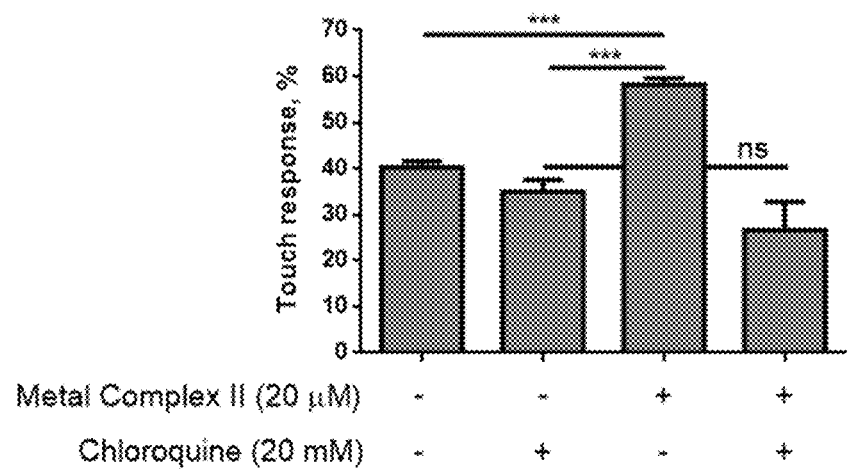
FIG. 8 shows how metal complex (II) is able to rescue neuronal impairment due to 110Q::TdTomato expression (3$^{rd}$ column from the left) compared to non-treated animals (expressing 110Q::TdTomato showing neuronal impairment) as a control (1$^{st}$ column from the left). Results presented as % of individuals showing touch response. However, when a specific inhibitor of autophagy like Chloroquine was used in combination with metal complex (II), no rescue was detected (column 4$^{th}$ from the left). Chloroquine does not induce additional touch response impairment (column 2$^{nd}$ from the left) to that due to 110Q::TdTomato expression (column 1$^{st}$ from left).

It was also tested whether this neuronal rescue effect is produced specifically by autophagy. This was done as explained in EXAMPLE 3, where the *C. elegans*' worms were incubated in the presence of metal complex (II) and chloroquine, which is a well-known inhibitor of autophagy. As FIG. 8 shows, animals cultured in the presence of both compounds are no longer rescued, suggesting that the beneficial effect of metal complex II is due to autophagy.

Another embodiment of present invention refers to the metal complexes comprising a compound of Formula (I) and at least one metal ion, described above herein, for use in the treatment of diseases related to defective proteasome activity.

Figure 3A:
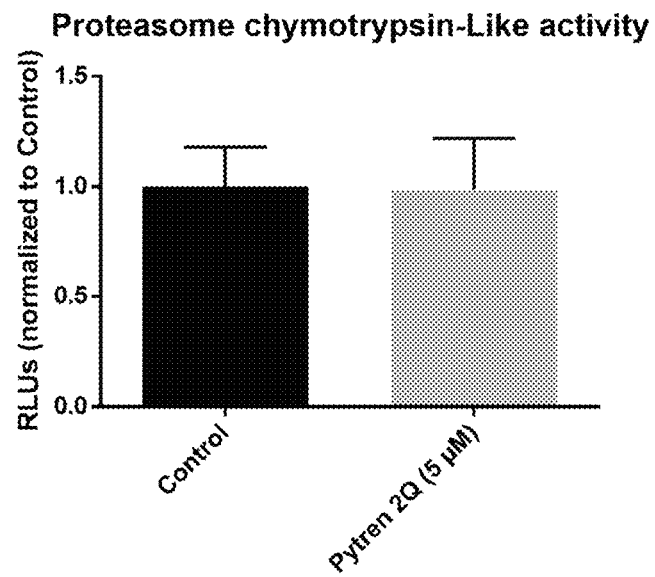
FIG. 3A shows the test carried out with Pytren 2Q also at 5 µM versus a control of non-treated cells. Pytren 2Q is, as metal complex (II), also a Mn(II) complex comprising a triazapyridinophane central structure, but wherein the quinolone heterocycle is linked by the 2-position to said triazapyridinophane central structure. The quinolone heterocycle in Pytren 2Q is thus linked to the triazapyridinophane central structure by the 2-position and not by the 4-position as in the metal complexes disclosed herein.

EXAMPLE 2 shows how the compounds of present invention, exemplified by metal complex (II) stimulate the proteasome activity (FIG. 3B). 2Q was also tested under the same test conditions. FIG. 3A shows that, in contrast to the activity shown by metal complex (II), compound 2Q does not stimulate proteasome activity.

Again, those results indicate that the structural difference between 2Q and metal complex (II), wherein the quinolone heterocycle is bonded to a triazapyridophane central structure by the 2-position, instead of by the 4-position, respectively, surprisingly provides to the selection of metal complexes disclosed herein with proteasome and/or autophagy activation.

One embodiment of present invention refers to a composition, or a pharmaceutical composition, comprising a metal complex comprising a compound of general formula (I) and at least one metal ion, as described above herein; together with at least one excipient or carrier, for use in the treatment of diseases related to the accumulation of intracellular deposits and/or diseases related to defective autophagy and/or defective proteasome activity.

For the purposes of present disclosure, acceptable excipients or carriers are water, saline solution, alcohols, polyethylene glycols, polyhydroxyethoxylated castor oil, peanut oil, olive oil, lactose, terra alba, glucose, fructose, mannitol, cyclodextrin, amylose, magnesium stearate, talc, gelatin, agar, pectin, starch, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, or polyvinylpyrrolidone, etc.

Another embodiment discloses a composition comprising an effective amount of a metal complex comprising a compound of general formula (I) and at least one metal ion, as described above herein, together with at least one excipient or carrier, for use in the treatment of diseases related to the accumulation of intracellular deposits and/or diseases related to defective autophagy and/or defective proteasome activity.

In general, an effective amount of the compound of interest is employed in treatment. The dosage of compounds used in accordance with the invention varies depending on the compound and the condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer.

Another embodiment of present invention refers to a composition for use, as described above herein, comprising an effective amount of a metal complex comprising a compound of general formula (I) and at least one metal ion, as described above herein, together with at least one excipient or carrier, for use in the treatment of diseases related to the accumulation of intracellular deposits and/or diseases related to defective autophagy and/or defective proteasome activity, wherein said composition further comprises, optionally, at least a second active compound.

Said second active compound corresponds to compounds used in the treatment of diseases related to the accumulation of intracellular deposits and/or diseases related to defective autophagy and/or defective proteasome activity, which includes, but is not limited to metformin, nucleic acids, antibodies, microRNA, antioxidants, polyphenolic compounds, dopaminergic inhibitors, cholinesterase inhibitors, riluzole, curcumin, and cell therapies.

Thus, an embodiment of present invention refers to a composition for use, as described above herein, wherein said second active ingredient is independently selected from metformin, a nucleic acid, an antibody, a microRNA, an antioxidant, a polyphenolic compound, a dopaminergic inhibitor, a cholinesterase inhibitor, riluzole or curcumin.

In one embodiment of present invention, the composition comprises an effective amount of a metal complex comprising a compound of general formula (I) and at least one metal ion, as described above herein, together with at least one excipient or carrier, wherein said metal ion is a divalent ion. More preferably, said divalent metal ion is selected from Cu(II), Fe(II), Zn(II) or Mn(II).

Another embodiment of present invention discloses a composition comprising an effective amount of a metal complex comprising a compound of general formula (I) and at least one metal ion, as described above herein, and at least one excipient or carrier, for use as described above herein, wherein said metal complex is metal complex (II).

Another embodiment of present invention discloses a composition as described above herein, for use in the treatment of diseases related to the accumulation of intracellular deposits and/or diseases related to defective autophagy and/or defective proteasome activity, wherein said diseases are age-related diseases.

One embodiment of present invention discloses a composition as described above herein, for use in the treatment of diseases which present accumulation of intracellular deposits. In a preferred embodiment said diseases are selected from Lafora disease, Adrenoleukodytrophy or Huntington disease, more preferably Lafora disease or Huntington disease.

Another embodiment of present invention discloses a composition comprising an effective amount of a metal complex comprising a compound of general formula (I) and at least one metal ion, as described above herein, together with at least one excipient or carrier, for use in the treatment of diseases related to the accumulation of intracellular deposits and/or diseases related to defective autophagy and/or defective proteasome activity, wherein said diseases are independently selected from Lafora disease or Huntington disease.

One embodiment discloses the use of a metal complex comprising a compound of general formula (I) and at least one metal ion, as described above herein, in the manufacturing of a drug for the treatment of diseases related to the accumulation of intracellular deposits and/or diseases related to defective autophagy and/or defective proteasome activity. Preferably said metal ion is a divalent ion, more preferably independently selected from Cu(II), Fe(II), Zn(II) or Mn(II).

Another embodiment discloses the use of a metal complex comprising a compound of general formula (I) and at least one metal ion, as described above herein, in the manufacturing of a drug for the treatment of diseases related to the accumulation of intracellular deposits and/or diseases related to defective autophagy and/or defective proteasome activity, wherein said metal complex is metal complex (II).

One embodiment of the disclosed invention provides a method of treatment comprising administering an effective amount of a metal complex comprising a compound of general formula (I) and at least one metal ion, as described above herein, to an individual suffering from diseases presenting accumulation of intracellular deposits and/or diseases related to defective autophagy and/or defective proteasome activity. Preferably said metal ion is a divalent ion, more preferably independently selected from Cu(II), Fe(II), Zn(II) or Mn(II).

One embodiment disclosed provides a method of treatment comprising administering an effective amount of a metal complex comprising a compound of general formula (I) and at least one metal ion, as described above herein, to an individual suffering from a disease related to the accumulation of intracellular deposits and/or a disease related to defective autophagy and/or defective proteasome activity, wherein said metal complex is metal complex (II).

EXAMPLES

EXAMPLE 1: Study of Autophagy Activation in Lafora Disease

Two lines of fibroblasts from healthy individuals (controls, C1 and C2) and three lines of fibroblasts from Lafora disease patients (L1 and L2, deficient in laforin; M1, deficient in malin) were tested.

All cell lines were taken from the Centro de Investigación Principe Felipe (CIPF) collection. All the cell lines used from Lafora patients, deficient in laforin [Aguado et al., 2010, Human Molecular Genetics 19, 2867-2876; Knecht et al., 2010, Autophagy, 6, 991-993] or malin [Criedo et al., 2012, Hum. Mol. Genetics 21, 1521-1533; Knecht et al., 2012, autophagy 8,701-703] have a deficit in autophagy.

1.1. Study of LC3-II Levels

As mentioned before, the level of the LC3-II protein is nowadays the best biomarker of autophagy activity.

It was assessed by Western Blot analysis, as described previously [Moruno-Manchon et al., Biochem. J. 449, 497-506] the levels of LC3-II in the cell lines mentioned above (C1, C2, L1, L2, M1, A1, A2 and A3) which were all incubated in complete medium and fasting media (i.e. partially removing the nutrients from the culture media). To determine the autophagy flow, lysosomal degradation has been inhibited (with 0.2 mM leupeptin and 20 mM $NH_4Cl$), as described [Fuertes et al., 2003 Biochem. J. 375, 75-86] allowing this way the accumulation of LC3-II protein. Antibodies against LC3 and against Actin, (which was used as charge control) were used.

Results Study 1:

Study 1 was carried out in cell lines C1 and C2 (healthy individuals), L1, L2 and M1 (Lafora patients), with and without treatment with 5 μM of metal complex (II).

The study was carried out in each case using complete media and using fasting media. Partially removing the nutrients from the culture media emulates a cell fasting state (fasting media) and provokes the cell to activate autophagy to obtain energy from degrading internal structures. As shown in FIG. 1, control fibroblasts (cell lines C1, C2), fibroblasts from Lafora patients (cell lines L1, L2 and M1 in FIG. 1A and cell lines L3 and M1 in FIG. 1B) have greater levels of LC3-II protein after the treatment with the metal complex (II), at a concentration of 5 μM during 6 hours. Results indicate therefore an increase of autophagy in both healthy and Lafora patient cell lines treated with metal complex (II).

Results study 2:

Levels of LC3-II on human fibroblasts (3349B and 3348D) healthy or with mutations in laforin (L1 and L2) and malin (M1) were tested in the absence (labelled as 1) or presence of metal complex II at 1 μM, 5 μM and 10 μM concentrations (labelled as 2, 3 and 4 respectively). Rapamycin was used as a positive control (labelled as 5).

As shown in FIG. 2, metal complex (II) at 1, 5 and 10 μM concentrations, improved autophagy defects when added to the media on human fibroblasts deficient in laforin and malin, wherein the amount of LC3-II indicates the level of autophagy activation.

1.2. Study of Number of Autophagic Vacuoles.

This test was carried out with the study of GFP-LC3 fluorescent transfected cells, in order to determine the levels of autophagy in cells treated with metal complex (II). Healthy human fibroblasts and fibroblasts from Lafora patients were transiently transfected with 0.5 μg of pEGFP-LC3 during 6 hours. Approximately 24 hours after transfection, part of the cells were treated with 5 μM metal complex (II) during 6 hours. During the last 90 minutes of the treatment lysosomal inhibitors (0.2 M leupeptin+20 mM $NH_4Cl$) were added.

As shown in FIG. 1C, metal complex (II) increased the number of autophagic vacuoles, and thus increased autophagy, in human fibroblasts (in both healthy human fibroblasts or human fibroblasts presenting Lafora disease).

Example 2: Study of Proteasome Chymotrypsin-Like Activation

Figure 3B:
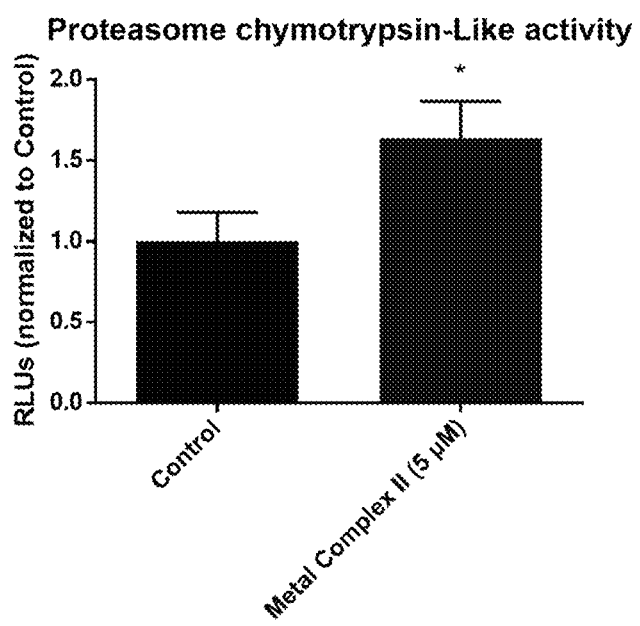
FIG. 3B shows the test carried out with metal complex (II) at 5 µM versus a control of non-treated cells.

In vitro studies to show the proteasome chymotrypsin-like activation with metal complex (II) in human dermal fibroblasts. Results are measured in relative luminescence units (RLUs) normalized to the control. FIG. 3B shows that treatment with metal complex (II), at a concentration of 5 µM, stimulates the proteasome chymotripsyn-like activity by 64.0±16.0% (p value=0.0103), when compared to the control non-treated primary human dermal fibroblasts. This study was carried out also with 2Q (FIG. 3A), which is Mn(II) complex also comprising a triazapyridinophane central structure, but wherein the quinolone heterocycle in 2Q is in bonded to the triazapyridinophane central structure by the 2-position and not by the 4-position as in the metal complexes disclosed herein. As shown in FIG. 3A, said compound did not show any significant effect upon proteasome activity.

The table below summarizes also the results of the test carried out with metal complex (II):

| Chart Analyzed | Met. Comp. II |
| --- | --- |
| Column B | Metal Complex (II) at 5 µM |
| vs. | vs, |
| Column A | CONTROL |
| Unpaired t test | |
| P value | 0.0103 |
| P value summary | * |
| Significantly different? (P < 0.05) | Yes |
| One- or two-tailed P value? | Two-tailed |
| t, df | t = 4.005 df = 5 |
| How big is the difference? | |
| Mean ± SEM of column A | 1.000 ± 0.1035 N = 3 |
| Mean ± SEM of column B | 1.640 ± 0.1134 N = 4 |
| Difference between means | 0.6398 ± 0.1597 |
| 95% confidence interval | 0.2291 to 1.050 |
| R square | 0.7624 |

This confirms that only the metal complexes disclosed herein, wherein the quinolone moiety is linked to the triazapyridinophane central structure by the 4-position are useful in the treatment of diseases related to the accumulation of intracellular deposits and/or diseases related to defective autophagy and/or defective proteasome activity.

Example 3: Response Activation in *C. elegans'* Huntington's Disease Model

The study was conducted to assess whether administration of metal complex (II) improves the neurosensitivity (gentle touch sensitivity) in *Caenorhabditis elegans'* (*C. elegans*) Huntington's disease model.

*C. elegans* detect and respond to diverse mechanical stimuli using neuronal circuitry. These stimuli include gentle touch stimulus delivered to the body, harsh touch to the midbody, harsh touch to the head or tail, nose touch and texture.

The initial and most generally used method to test for gentle touch sensitivity is to stroke animals with an eyebrow hair that has been glued to the end of a toothpick (FIG. 4).

*C. elegans* expressing 110CAG fused in frame with TdTomato in mechanosensory neurons aggregate and induced neural impairment were used. FIG. 5A shows a confocal image of the head of a *C. elegans* transgenic worm showing 110Q::TdTomato expression in FLP mechanosensory neurons (shown circled). The tissue in light grey is the marker for transgenesis (i.e. green fluorescent protein (GFP) expressed in the pharynx). FIG. 5B shows a confocal image with the detail showing the FLP neurons expressing 110Q::TdTomato aggregates (shown circled).

*C. elegans* neuronal impairment is shown in FIG. 5C, where three independent strains expressing 110Q::TdTomato were tested using touch assays, as described above for FIG. 4. All the three strains tested expressing 110Q::TdTomato showed neuronal impairment (lower mechanosensation shown as % of individuals showing touch response), as seen in FIG. 5C, when compared to the results of wildtype animals (labelled as WT).

FIG. 5D shows how metal complex (II) is able to rescue neuronal impairment, due to 110Q::TdTomato expression, in a dose-dependent manner. The test was carried out using non-treated animals (expressing 110Q::TdTomato and thus showing neuronal impairment) as a control C, and animals treated with Metformin at 2 mM were used as a positive control. The results are based on the three experimental replicates shown in FIG. 6z. Each test was carried out treating animals (expressing 110Q::TdTomato showing neuronal impairment) with 5, 10 and 20 µM concentrations of metal complex (II), using non-treated animals as a control and animals treated with Metformin at a concentration of 2 mM as a positive control.

FIG. 7 shows how metal complex (II) is able to rescue neuronal impairment due to 110Q::TdTomato expression in a dose-dependent manner versus compound 2Q which does not produce any significant change in the tested doses. The test was carried out using non-treated animals (expressing 110Q::TdTomato showing neuronal impairment) as a control C. Metformin was again used as a positive control. Again, these data indicate that only the selection of metal complexes disclosed herein, wherein the quinolone moiety is linked to the triazapyridinophane central structure by the 4-position are useful in the treatment of diseases related to the accumulation of intracellular deposits and/or diseases related to defective autophagy and/or defective proteasome activity.

Finally, it was tested whether the rescue of the neuronal impairment due to 110Q::TdTomato expression shown with the treatment of metal complex (II) is produced by activation of autophagy. To this end, the worm *C. elegans* (expressing 110Q::TdTomato showing neuronal impairment) was incubated in the presence of metal complex (II) with and without the presence of chloroquine, a well-known inhibitor of autophagy. As control, animals (expressing 110Q::TdTomato showing neuronal impairment) were also incubated with and without the presence of chloroquine but without treatment with metal complex (II). As FIG. 8 shows, animals cultured in the presence of both compounds are no longer rescued, suggesting that the beneficial effect of metal complex II is due to autophagy and not to other possible mechanisms.

Example 4: Acute Toxicity, In Vivo, of a Metal Complex of Formula (I)

To evaluate the acute toxicity metal complex (II) was administered in vivo to a total of 12 mice divided in 4 groups of 3 mice. Male and female mice bodyweight was between 24 to 30 g and 17 to 22 g respectively. Metal complex (II) was administered to the mice orally together with a phosphate saline buffer (PBS) or with NaCl 0.9%.

Acute toxicity experiments showed neither death, nor reduced locomotor activity in the tested mice (males and females) at doses up to 200 mg/kg administered orally, either in PBS or in NaCl at 0.9%.

The invention claimed is:

1. A method of treating diseases related to the accumulation of intracellular deposits, and/or diseases related to defective autophagy and/or defective proteasome activity, wherein said diseases are independently selected from the group consisting of: Huntington disease, Prion disease, Amyloidoses diseases, Focal segmental glomerulosclerosis, diseases related to an Alpha-1 antitrypsin (AAT) deficiency, sphingolipidoses, Niemann-Pick type C disease (NPC), Wolman disease and Cholesteryl Ester Storage Diseases (CESD), glycogen storage diseases, galactosemia, hereditary fructose intolerance, muccopolysaccharidoses, disorders of pyruvate metabolism, phosphoglycerate kinase deficiency, Lafora disease, Adrenoleukodystrophy, Autophagic Vacuolar Myopathies, Danon's disease, Cerebral Cavernous Malformation (CCM), Granular corneal dystrophy type 2 (GCD2), Chronic Kidney Disease (CKD), Bethlem myopathy, Ullrich congenital muscular dystrophy, Myosclerosis, inclusion body myositis, HIV, adenovirus, hepatitis B, Sjogren's syndrome, and metabolic acidosis, said method comprising administering, to a subject in need thereof, an effective amount of a metal complex comprising a compound of general formula (I)

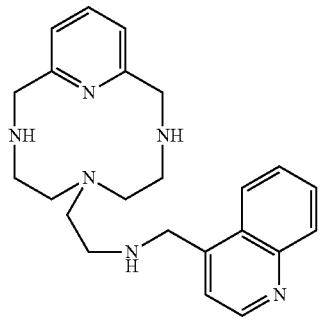

Formula (I)

and at least one metal ion.

2. The method according to claim 1, wherein said metal ion is a divalent metal ion.

3. The method according to claim 2, wherein said divalent metal ion is selected from the group consisting of Cu(II), Fe(II), Zn (II) and Mn(II).

4. The method according to claim 3, wherein said divalent metal ion is Mn(II).

5. A method of treating diseases related to the accumulation of intracellular deposits, and/or diseases related to defective autophagy and/or defective proteasome activity, wherein said diseases are selected from the group consisting of Lafora disease, Adrenoleukodystrophy, and Huntington disease, said method comprising administering, to a subject in need thereof, an effective amount of a metal complex comprising a compound of general formula (I)

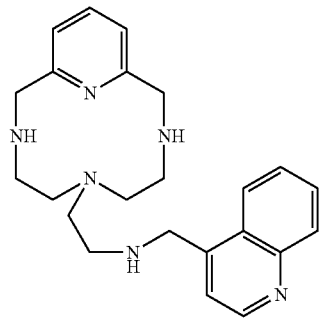

Formula (I)

and at least one metal ion.

6. A method of treating diseases related to the accumulation of intracellular deposits, and/or diseases related to defective autophagy and/or defective proteasome activity, wherein said diseases are selected from the group consisting of Lafora disease, Adrenoleukodytrophy, and Huntington disease, said method comprising administering, to a subject in need thereof, an effective amount of a composition containing an effective amount of a metal complex comprising a compound of general formula (I)

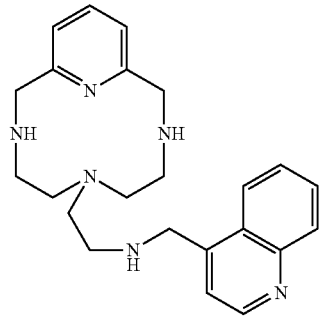

Formula (I)

and at least one metal ion.

7. The method according to claim 5, wherein said metal ion is a divalent metal ion.

8. The method according to claim 7, wherein said divalent metal ion is selected from the group consisting of Cu(II), Fe(II), Zn (II), and Mn(II).

9. The method according to claim 8, wherein said divalent metal ion is Mn(II).

10. The method according to claim 6, wherein said composition further comprises a second active ingredient.

11. The method according to claim 10, wherein said second active ingredient is independently selected from: metformin, a nucleic acid, an antibody, a microRNA, an antioxidant, a polyphenolic compound, a dopaminergic inhibitor, a cholinesterase inhibitor, riluzole or curcumin.

12. The method according to claim 6, wherein said metal ion is a divalent metal ion.

13. The method according to claim 12, wherein said divalent metal ion is selected from the group consisting of Cu(II), Fe(II), Zn(II), and Mn(II).

* * * * *

UNITED STATES PATENT AND TRADEMARK OFFICE
CERTIFICATE OF CORRECTION

PATENT NO. : 11,013,732 B2
APPLICATION NO. : 16/621782
DATED : May 25, 2021
INVENTOR(S) : José Luis Mullor Sanjosé et al.

It is certified that error appears in the above-identified patent and that said Letters Patent is hereby corrected as shown below:

In the Specification

Column 7, Line 34: are selected from Lafora disease, Adrenoleukodytrophy or
Should read: are selected from Lafora disease, Adrenoleukodystrophy or Column 11, Line 14: selected from Lafora disease, Adrenoleukodytrophy or Hun-
Should read: selected from Lafora disease, Adrenoleukodystrophy or Hun- In the Claims Column 16, Line 21, Claim 6: of Lafora disease, Adrenoleukodytrophy, and Huntington
Should read: of Lafora disease, Adrenoleukodystrophy, and Huntington Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*